(12) United States Patent
Rasheed

(10) Patent No.: US 9,593,538 B2
(45) Date of Patent: Mar. 14, 2017

(54) CIRCUMFERENTIAL AND LONGITUDINAL CUTTER COVERAGE IN CONTINUATION OF A FIRST BIT DIAMETER TO A SECOND EXPANDABLE REAMER DIAMETER

(71) Applicant: Wajid Rasheed, Slough (GB)

(72) Inventor: Wajid Rasheed, Slough (GB)

(*) Notice: Subject to any disclaimer, the term of this patent is extended or adjusted under 35 U.S.C. 154(b) by 0 days.

(21) Appl. No.: 14/295,717

(22) Filed: Jun. 4, 2014

(65) Prior Publication Data

US 2014/0311802 A1 Oct. 23, 2014

Related U.S. Application Data

(62) Division of application No. 13/949,286, filed on Jul. 24, 2013, which is a division of application No. 12/966,195, filed on Dec. 13, 2010, now Pat. No. 8,511,404.

(51) Int. Cl.

| | |
|---|---|
| *E21B 10/32* | (2006.01) |
| *E21B 44/00* | (2006.01) |
| *E21B 47/01* | (2012.01) |
| *E21B 47/08* | (2012.01) |
| *A01N 43/40* | (2006.01) |
| *E21B 47/09* | (2012.01) |

(52) U.S. Cl.
CPC ............ *E21B 10/32* (2013.01); *E21B 47/08* (2013.01); *A01N 43/40* (2013.01); *E21B 10/322* (2013.01); *E21B 44/00* (2013.01); *E21B 47/01* (2013.01); *E21B 47/082* (2013.01); *E21B 47/09* (2013.01)

(58) Field of Classification Search
CPC ........ E21B 10/322; E21B 10/32; E21B 10/56; E21B 10/46; E21B 10/26; E21B 2010/562; E21B 2010/561; E21B 2010/565; E21B 2010/566; E21B 10/567
USPC ........ 175/265, 266, 263, 286, 287, 289, 279, 175/384
See application file for complete search history.

(56) References Cited

U.S. PATENT DOCUMENTS

| | | |
|---|---|---|
| 904,344 A | 11/1908 | Maples |
| 1,302,058 A | 4/1919 | Layne et al. |
| 1,667,190 A | 4/1928 | Campbell |
| 1,810,201 A | 6/1931 | Campbell |
| 1,902,174 A | 3/1933 | Lewis et al. |
| 1,989,476 A | 1/1935 | Evans |
| 2,026,323 A | 12/1935 | Reed |
| 2,028,910 A | 1/1936 | Macclatchie |
| 2,084,737 A | 6/1937 | Magnus |
| 2,122,863 A | 7/1938 | Howard et al. |
| 2,488,003 A | 11/1939 | Creighton et al. |
| 2,712,434 A | 7/1955 | Giles et al. |
| 2,859,943 A | 11/1958 | Chadderdon |

(Continued)

OTHER PUBLICATIONS

Wajid Rasheed et al. SPE 92623 Reducing Risk and Cost in Diverse Well Construction Applications: Eccentric Device Drills Concentric Hole and Offers a Viable Alternative to Underreamers SPE/IADC Drilling Conference Held Feb. 23-25, 2005.

(Continued)

*Primary Examiner* — Blake Michener
*Assistant Examiner* — Kipp Wallace

(57) ABSTRACT

The Smart Reamer® Tool, Apparatus or Method is used to underream an oil or natural gas well and deliver a desired wellbore diameter without the need to unnecessarily stop drilling or trip out of the hole.

20 Claims, 7 Drawing Sheets

(56) References Cited

U.S. PATENT DOCUMENTS

| | | | | |
|---|---|---|---|---|
| 3,068,946 | A | 12/1962 | Frisby et al. | |
| 3,237,705 | A | 3/1966 | Williams | |
| 3,376,942 | A | 4/1968 | Van Winkle | |
| 3,431,989 | A | 3/1969 | Waterman et al. | |
| 3,561,549 | A | 2/1971 | Garrison et al. | |
| 3,753,470 | A | 8/1973 | Lagerstrom et al. | |
| 4,011,918 | A * | 3/1977 | Jurgens | E21B 17/02 175/325.2 |
| 4,031,974 | A | 6/1977 | Peterson | |
| 4,552,232 | A | 11/1985 | Frear | |
| 4,807,708 | A | 2/1989 | Forrest et al. | |
| 4,848,490 | A | 7/1989 | Anderson | |
| 4,889,197 | A | 12/1989 | Boe | |
| 4,982,802 | A | 1/1991 | Warren et al. | |
| 5,027,914 | A * | 7/1991 | Wilson | E21B 10/26 166/55.6 |
| 5,029,656 | A | 7/1991 | Ivie | |
| 5,141,062 | A | 8/1992 | Anderson | |
| 5,314,033 | A | 5/1994 | Tibbitts | |
| 5,341,888 | A * | 8/1994 | Deschutter | E21B 10/322 175/323 |
| 5,368,114 | A | 11/1994 | Tandberg et al. | |
| 5,373,900 | A * | 12/1994 | Lynde | B23B 5/16 166/297 |
| 5,377,773 | A | 1/1995 | Tibbitts | |
| 5,423,389 | A | 6/1995 | Warren et al. | |
| 5,495,899 | A | 3/1996 | Pastusek et al. | |
| 5,531,281 | A | 7/1996 | Murdock | |
| 5,979,570 | A | 11/1999 | Mcloughlin et al. | |
| 6,041,874 | A | 3/2000 | Lee | |
| 6,123,160 | A | 9/2000 | Tibbitts | |
| 6,123,161 | A | 9/2000 | Taylor | |
| 6,279,670 | B1 | 8/2001 | Eddison et al. | |
| 6,283,233 | B1 | 9/2001 | Lamine | |
| 6,325,162 | B1 | 12/2001 | Eppink et al. | |
| 6,378,632 | B1 | 4/2002 | Dewey | |
| 6,439,318 | B1 | 8/2002 | Eddison et al. | |
| 6,668,949 | B1 | 12/2003 | Rives | |
| 6,695,080 | B2 | 2/2004 | Presley | |
| 6,708,785 | B1 | 3/2004 | Russell et al. | |
| 6,732,817 | B2 | 5/2004 | Dewey et al. | |
| 6,739,416 | B2 | 5/2004 | Presley et al. | |
| 7,004,266 | B2 | 2/2006 | Russell et al. | |
| 7,036,611 | B2 | 5/2006 | Radford et al. | |
| 7,252,163 | B2 | 8/2007 | Ollerenshaw et al. | |
| 7,451,837 | B2 | 11/2008 | Hoffmaster et al. | |
| 7,493,971 | B2 | 2/2009 | Nevlud et al. | |
| 7,757,787 | B2 | 7/2010 | Mackay et al. | |
| 7,770,664 | B2 | 8/2010 | Laird et al. | |
| 7,823,663 | B2 | 11/2010 | Eddison | |
| 7,861,809 | B2 | 1/2011 | Gavia et al. | |
| 8,172,009 | B2 | 5/2012 | Hall et al. | |
| 8,281,880 | B2 | 10/2012 | Hall et al. | |
| 8,365,820 | B2 | 2/2013 | Hall et al. | |
| 8,365,821 | B2 | 2/2013 | Hall et al. | |
| 8,550,188 | B2 | 10/2013 | Makkar et al. | |
| 8,770,321 | B2 | 7/2014 | Makkar et al. | |
| 8,776,912 | B2 | 7/2014 | Makkar et al. | |
| 2002/0017402 | A1 * | 2/2002 | Bird | 175/426 |
| 2003/0029644 | A1 * | 2/2003 | Hoffmaster et al. | 175/263 |
| 2005/0145417 | A1 | 7/2005 | Radford et al. | |
| 2005/0241856 | A1 | 11/2005 | Lassoie et al. | |
| 2005/0274546 | A1 | 12/2005 | Fanuel et al. | |
| 2006/0113113 | A1 | 6/2006 | Underwood et al. | |
| 2006/0195307 | A1 * | 8/2006 | Huang et al. | 703/7 |
| 2007/0089912 | A1 | 4/2007 | Eddison et al. | |
| 2008/0128174 | A1 | 6/2008 | Radford et al. | |
| 2008/0128175 | A1 | 6/2008 | Radford et al. | |
| 2008/0251295 | A1 | 10/2008 | Lassoie et al. | |
| 2009/0114448 | A1 * | 5/2009 | Laird et al. | 175/61 |
| 2010/0018779 | A1 * | 1/2010 | Makkar | E21B 10/322 175/382 |
| 2010/0116556 | A1 | 5/2010 | Buske | |
| 2010/0276201 | A1 * | 11/2010 | Makkar et al. | 175/57 |
| 2010/0282511 | A1 * | 11/2010 | Maranuk et al. | 175/40 |
| 2012/0193147 | A1 | 8/2012 | Hall | |
| 2012/0211280 | A1 | 8/2012 | Dewey | |
| 2012/0273187 | A1 | 11/2012 | Hall | |
| 2012/0298423 | A1 | 11/2012 | Cruickshank | |
| 2013/0206401 | A1 | 8/2013 | Bhoite | |
| 2014/0102797 | A1 | 4/2014 | Mahajan | |
| 2014/0131109 | A1 | 5/2014 | Mahajan | |
| 2014/0262508 | A1 | 9/2014 | Fuller | |
| 2014/0262525 | A1 | 9/2014 | Fuller | |

OTHER PUBLICATIONS

Wajid Rasheed et al. Norwegian operators reap rewards by controlling inclination in rotary mode Drilling Contractor Magazine http://www.drillingcontractor.org/dc-archive/januaryfebruary-2000 Jan./Feb. 2000.

Wajid Rasheed et al. Underreaming advances E & P Magazine http://www.epmag.com/EP-Magazine/archive/Underreaming-advances_2474 Editor, Latin America Tuesday, May 4, 2004.

Wajid Rasheed et al. Underreaming Technologies Provide Array of Applications Oil & Gas Journal http://www.ogj.com/articles/print/volume-98/issue-8/special-report/underreaming-technologies-provide-array-of-applications.html.

\* cited by examiner

CIRCUMFERENTIAL AND LONGITUDINAL CUTTER COVERAGE IN CONTINUATION OF A FIRST BIT DIAMETER TO A SECOND EXPANDABLE REAMER DIAMETER

CROSS-REFERENCE TO RELATED APPLICATIONS

This application is a divisional of U.S. Ser. No. 13/949,286 which is a divisional of U.S. Ser. No. 12/966,195 filed 13 Dec. 2010 and continuation-in-part of WO 2009/PCT 156552 A1 filed 27 Jun. 2009 claiming priority to GB 0811815.0 (27 Jun. 2008).

This application entitled "CIRCUMFERENTIAL AND LONGITUDINAL CUTTER COVERAGE IN CONTINUATION OF A FIRST BIT DIAMETER TO A SECOND EXPANDABLE REAMER DIAMETER" is a divisional of co-pending U.S. patent application Ser. No. 13/949,286 filed Jul. 24, 2013, which is a continuation of U.S. Ser. No. 12/966,195 filed Dec. 13, 2010, and entitled "DRILLING TOOL, APPARATUS AND METHOD FOR UNDERREAMING AND SIMULTANEOUSLY MONITORING AND CONTROLLING WELLBORE DIAMETER", which is a continuation-and-part of International Application number PCT/ES09/70261, filed Jun. 27, 2009 and entitled "DRILLING TOOL AND METHOD FOR WIDENING AND SIMULTANEOUSLY MONITORING THE DIAMETER OF WELLS AND THE PROPERTIES OF THE FLUID", and claims priority to and the benefit of GB 0811815.0, filed Jun. 27, 2008 and entitled "EXPANSION AND CALIPER TOOL", the entireties of which applications are hereby incorporated by reference as if fully set forth herein.

FIELD OF THE INVENTION

This invention relates primarily but not exclusively to a helical cutter element pattern for use in an underreaming tool that is capable of enlarging borehole diameters, especially wellbores in the oil and gas industry. The tool finds particular use as an underreaming tool, but can also be configured without cutting elements to provide downhole centralization, directional stabilisation, or as a means for expanding tubulars.

It is to be understood that the term 'expansion' as used herein refers to the capacity of the tool to expand outwardly towards and against the interior wall or walls of a passage, such as a borehole, especially a wellbore, or a tubular, and then to apply pressure or a cutting action against the wall or walls. It is not always essential that the passage itself be expanded, since the tool can be used for centralisation or stabilisation or like purposes without necessarily expanding the passage.

Other aspects of the invention include a method of placing cutters on an underreaming block to enlarge a passage; an expandable cutter block suitable for use in such a tool; a method of circumferentially distributing cutters to increase arc length along and around the wellbore, a method of wrapping cutters from a first fixed bit diameter to a second expandable diameter on an expandable block along and around a wellbore.

BACKGROUND OF THE INVENTION

Variations in well profile exist according to vertical, slant, directional and horizontal trajectories. Measurement may involve the acquisition and communication to surface of various types of wellbore data such as resistivity, porosity, permeability, azimuth, inclination and borehole diameter or rugosity, formation dips or bedding angles.

Previously, the underreamer and bit have been considered as separate tools, each involved in distinct functions. Typically, underreaming can involve several runs to achieve the desired wellbore diameter, after the bit has drilled the section. The time-lag between underreaming and drilling, therefore could easily exceed 48 hours depending on the depths involved. If the actual hole diameter did not match the planned diameter, casing tolerances would not be met and therefore a corrective run would be required and the whole cycle of underreaming would need to be repeated.

In the aspects of cutter element placement and nozzle location the present invention is differentiated from and shows advantages over the prior art. A major drawback of prior art underreamers is their cutting performance in terms of maintaining similar rates of penetration to the bit. To one skilled in the art, it is known that the bit has optimized cutter element placements and nozzle locations, and this often leads to the bit outperforming the underreamer. Consequently, this leads to either a separate underreaming run after drilling the section, or leads to the underreaming-while-drilling itself taking several attempts before a complete section is underreamed satisfactorily.

In terms of drilling dynamics, the optimised drill-bit drills at a faster rate of penetration than the underreamer which has trouble maintaining similar rates of penetration. Due to the distances between the bit and underreamer which may be 120 ft (36 m) or more, the bit may have exited a hard formation or layer while the underreamer may just be entering the earlier hard formation or hard layer as it is may not be connected directly to the bit. The prior art underreamers have limited cutter elements in contact with the wellbore and limited nozzle cleaning action due to the location of nozzles outside the cutter block elements.

Further the prior art generates time-consuming cycles of entry and exit into the well-bore.

Further the prior art has limited cutter elements in contact with the wellbore.

Further the prior art has limited practical application of a mechanical caliper outside the cutter block.

To those skilled in the art, it is known that the industry relies on even more rudimentary and time-consuming indicators of verification such as an increase in drilling torque as cutters interact with the formation or even pulling up the drill-string and underreamer to the previous hole size in order to see whether the top-drive stalls as the bottom-hole assembly gets stuck due to the expanded tool.

SUMMARY OF THE INVENTION

The present invention seeks to optimize underreaming and bit performance using novel cutter placements that provide continuation from a first bit diameter to a second expandable diameter.

It is a further object to provide a novel cutter insert layout that provides for improved underreaming and reduces the need for corrective underreaming runs by increasing the percentage of cutters in contact with the wellbore.

In accordance with the aspect that concerns cutter element placement, it can be seen that these are located in rows extending diagonally across the face of the cutter block, and helically in respect of the wellbore.

The helix can be oriented in a sense which, corresponds to the path of a screw advancing down the wellbore, although by no means at a corresponding screw pitch and due to the cutter elements may be used to underream upward.

The helix is also in alignment and considered synchronised with the extended outer ends of the rows of teeth on the drill bit, if notionally wrapped in continuation of that alignment around the outside of the BHA extending back as far as the tool body.

This provides the advantage that, as can be seen when viewed along the wellbore, the cutter inserts engage the wellbore over a much better circumferentially distributed arc than the six parallel lines of the traditional arrangements, with consequent benefits to equalization of forces around the tool and therefore around the BHA, of which the tool is a part.

It is thus an object of the present invention to provide expandable underreamer cutters aligned and considered synchronised with the extended outer ends of the rows of teeth of a first fixed bit diameter to a second expandable diameter, with a directional control system such as a rotary steerable.

It is a further object of the invention to enable expandable underreamer cutters to be superimposed on a bit.

Alternatively or additionally expandable underreamer cutters can be wrapped around the wellbore in a notional view.

Although underreaming is a principal route to wellbore enlargement, the invention envisages alternative enlargement means similarly integrated including expandable bits.

It is a further object to provide an internal duct to an expandable block providing fluid flow to an external surface preferably by a nozzle located among, beside, between, below or within rows of cutters.

It is a further object to provide a tool capable of simultaneously conducting well-bore enlargement, taking caliper measurements preferably by a sensor located within, beside or in between rows of cutters.

These and other objects will emerge from the following description and the appended claims.

In one aspect, the invention provides for helical pattern of cutters arranged as elements or inserts on a number of expandable blocks located within a tool body, means for attaching the tool body directly or indirectly to a support whereby it can be rotated and moved axially along a borehole below a restriction, at least one expandable block adapted to be extendable from the tool body to an expansion diameter greater than the restriction. The support may typically be a drill string or an extended length of coiled tubing, as used in downhole operations in oil and gas fields.

In preferred embodiments of the invention, the expansion operation is an underreaming application, and expansion elements comprise a set of cutter blocks optimally configured with cutter inserts and nozzles.

In yet another alternate configuration, the same blocks may simply bear against the underreamed wellbore in order to stabilize the tool within the wellbore without enlarging the bore. The same blocks may be received within an additional section of the tool or a separate steel body suitably prepared to provide a means of stabilization to the expansion operation.

Alternatively, the same blocks may be received within an additional section of the tool or a separate steel body suitably prepared to provide a means of stabilization for underreaming applications.

It is to be noted that the description herein of the structure and operation of cutter or expansion blocks is applicable generally, irrespective of function, except to the extent that cutter inserts may be provided specifically for underreaming purposes and removed for stabilisation purposes.

The tool body is typically a cylindrical high grade steel housing adapted to form part of a bottom-hole assembly (BHA). Thus the means for attaching the tool body to the support, whether it is a drill string or coiled tubing, may comprise a screw thread provided on the tool body which is engageable with a drill collar. The attachment to the drill string need not be direct, but may be indirect, as there will typically be many different functional elements to be included in the long and narrow BHA, and the arrangement of the successive elements may vary.

The lower end of the BHA may be the drill bit, or a bull nose, and in between there may be a means for directional control such as a rotary steerable system. The tool body may be provided with a through passage for the flow of drilling fluid from the drill string.

The set of cutters may comprise a cutter block carrying a plurality of cutter elements directed outwardly of the tool body. The cutter block may be received within the tool body in a cutter block chamber having an open mouth, and the cutter may be extendable from the chamber through the chamber mouth with the cutter elements projecting from the tool body, and retractable back into the chamber. The cutter elements may be polydiamondcrystalline inserts, or other inserts according to requirements.

The tool may then be provided with means for extending and retracting the cutter block from and into the cutter block chamber.

Hydraulic locking means may be provided to resist retraction of the extended cutter block into the cutter block chamber when the extension of the cutter block is opposed by external pressure. This may comprise a port from a source of drilling fluid into the cutter block chamber behind the cutter block.

The tool normally comprises a plurality of such cutter blocks, arranged symmetrically around the tool. Two cutter blocks would be on opposite sides of the tool, three blocks would be separated by 120 degrees, four by ninety degrees, and six by sixty degrees. In operation, the underreaming tool is typically rotated on the drill string as well as being moved axially along the wellbore.

In accordance with an aspect of the invention, the cutter block is provided with an internal duct for directing drilling fluid from a source to an external nozzle among the cutter elements. The source of drilling fluid may be the drill-string or other support for the tool, and the aforementioned through passage for the flow of drilling fluid from the drill string to the drill bit.

Alternatively or additionally, the tool body may be provided with an internal duct receiving a source of drilling fluid flowing to an external nozzle adjacent the set of cutters. In each case, the nozzle provides a fluid flow that can help to keep the cutters clean and prevent the build-up of clogging debris from the reaming operation, remove such material altogether from the underreaming zone, and provide a cooling and lubricating function for the cutters.

In another aspect the present invention incorporates a non-mechanical means of measurement which is practically applicable and may be an acoustic caliper.

In another aspect of the present invention housing for a mechanical caliper is provided within the cutter block which offers a robust location.

A mechanical caliper may be located within the cutter block optimally located among the most radially extended cutter elements or surface.

In a further aspect, the invention provides a method of operating an expansion tool to enlarge a borehole or tubular or the like to a target dimension below a restriction, which comprises locating a tool according to the invention in a borehole on a support below a restriction, extending the expansion element to an expansion diameter greater than the restriction, in a preferred embodiment extending a set of cutters to an underreaming diameter greater than the restriction, rotating the tool and moving it axially along the borehole on the drill string or other support, measuring the bore diameter by the caliper means, and continuing the expansion operation until the target dimension is achieved.

The expansion block means may comprise a cutter block carrying cutter elements directed outwardly of the tool body.

In another aspect, the invention provides an expansion tool comprising a tool body and an expansion block, optionally but not limited to a cutter block carrying a plurality of cutter elements directed outwardly of the tool body, wherein the expansion block is received within the tool body in an expansion block chamber having an open mouth, and means for extending the expansion block from the chamber through the chamber mouth, in the case of a cutter block with the cutter elements projecting from the tool body, and for retracting the expansion block back into the chamber, comprising cutters on a cutter block wherein cutters engage the wellbore at the same longitudinal or axial location but different radial positions, or wherein cutters engage the wellbore at different longitudinal or axial locations but the same radial position as seen from the central axis of the tool.

In a further aspect, the present invention seeks to optimise the cutter element placement, and may use a helical arrangement so as to offer a much higher percentage of underreaming cutters to engage the wellbore and formation.

Another novel aspect of the present invention is the location of nozzles to clean and lubricate cutter faces as well as evacuate cuttings build up within the wellbore. These two aspects allow the present invention to address the problems associated with prior art underreamers.

In a still further aspect, the invention provides an underreaming tool comprising a tool body and a cutter block carrying a plurality of cutter elements directed outwardly of the tool body, wherein the cutter block is received within the tool body in a cutter block chamber having an open mouth, and means for extending the cutter block from the chamber through the chamber mouth with the cutter elements projecting from the tool body, and for retracting the cutter block back into the chamber, wherein the cutter block is provided with an internal duct open to a source of drilling fluid to an external nozzle among, between, below or beside the cutter elements.

Aspects of the invention including a novel helical cutter insert pattern and novel disposition of nozzles for the delivery of fluid to the expansion or underreaming zone, are disclosed in the following specific description of exemplary embodiments of the invention.

BRIEF DESCRIPTION OF THE DRAWINGS

Embodiments of the invention are illustrated by way of non-limiting examples in the accompanying drawings, in which.

DETAILED DESCRIPTION OF THE INVENTION

Figure 1:
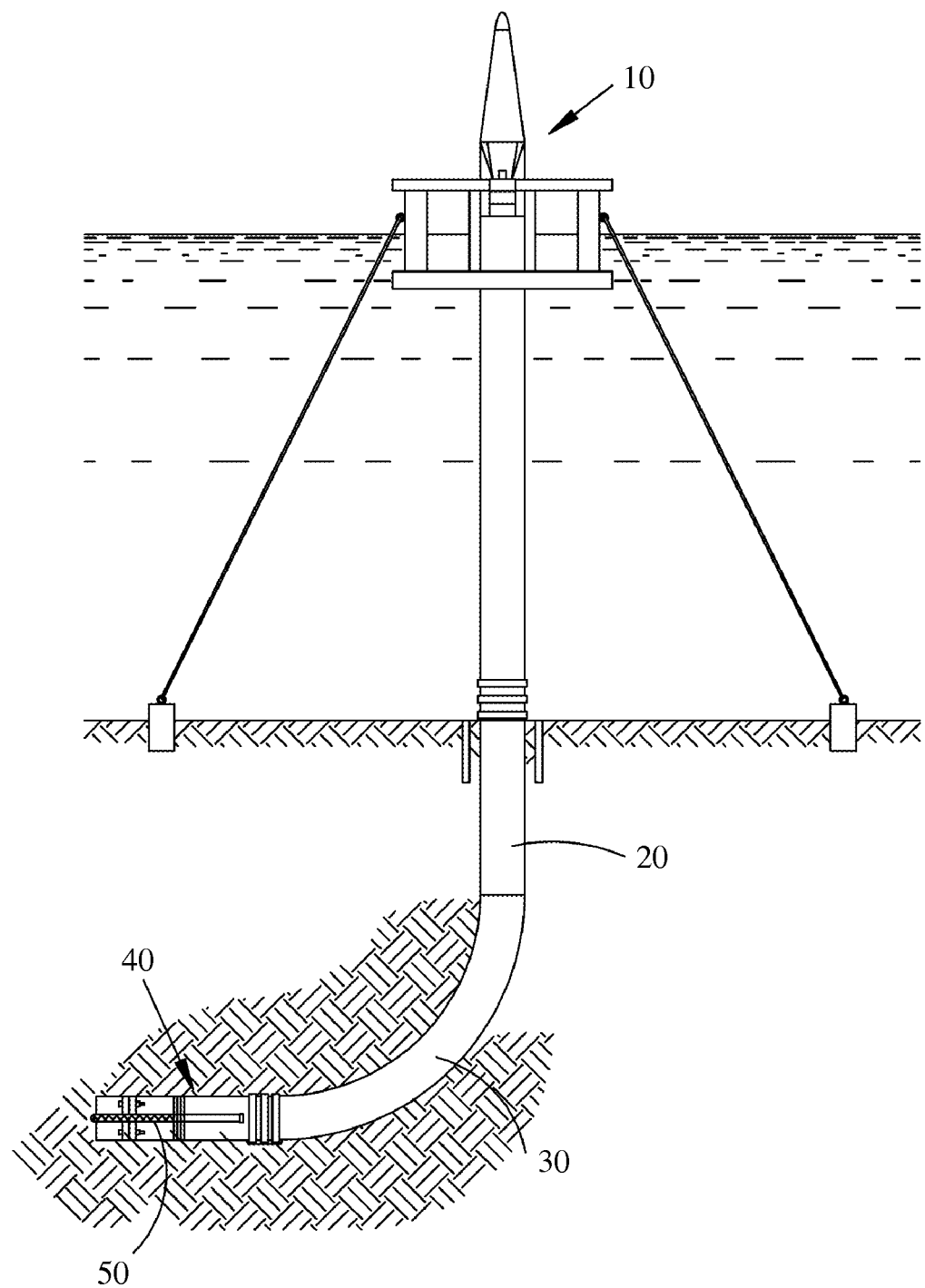
FIG. 1 is a general diagrammatic view of an oil or gas well showing surface structures and the underground wellbore, with a tool in accordance with the invention as part of a bottomhole assembly.

As shown in FIG. 1, an exemplary exploration or production rig comprises a surface structure 10 at the wellhead, a wellbore 20, and a drill string 30 in the wellbore with a bottom-hole assembly 40 at its lower end. The bottom-hole assembly includes an underreamer 50 in accordance with the invention, and a drill-bit (not shown).

Figure 2A:
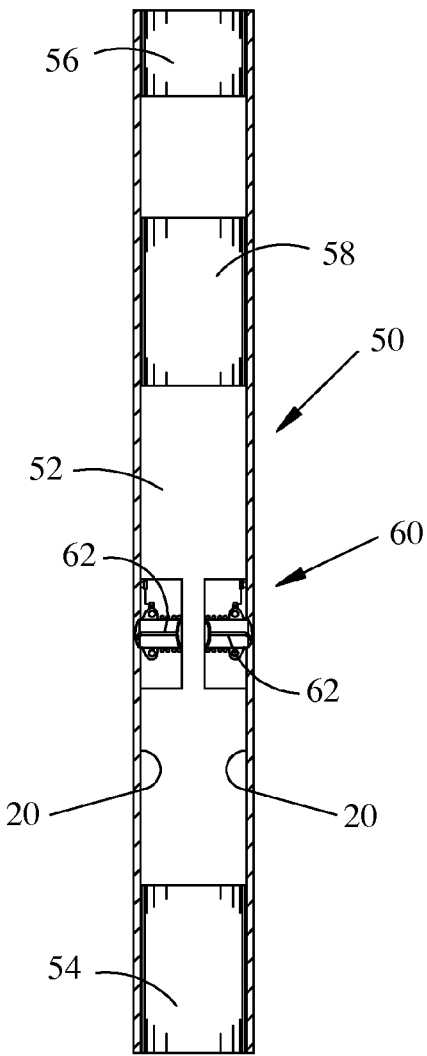
FIG. 2A is a side elevation, part cut away to show the expansion elements in a deactivated state, of the tool of FIG. 1.
Figure 2B:
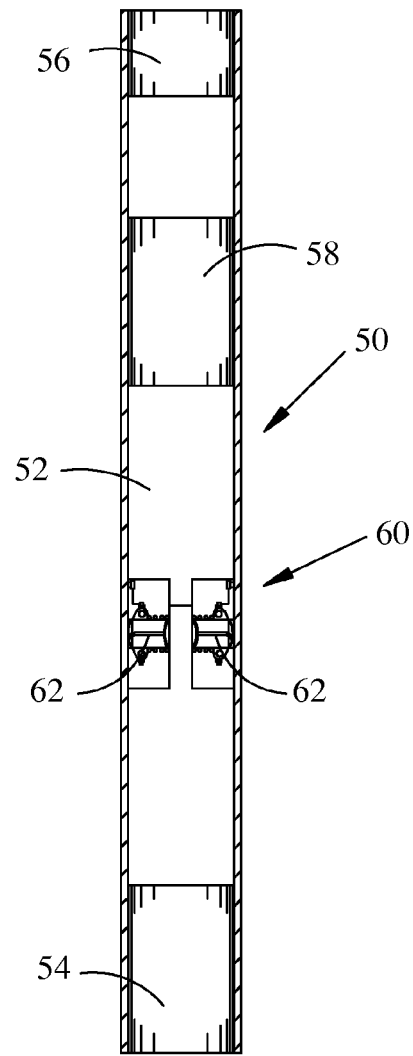
FIG. 2B is a side elevation corresponding to FIG. 2a showing the expansion elements in an activated state.

The underreamer 50 is illustrated in FIGS. 2A and 2B, and comprises a tubular steel body 52 provided with a drilling collar 54 at its downhole end and a mud-pulser 56 at its other end, which is adapted to be engaged by a further drill collar (not shown) to connect it other elements of the bottom-hole assembly 40, and then to the drill string 30.

The tool body also carries an acoustic caliper 58 and an expansion element assembly 60 between the acoustic caliper and the drill collar 54. The expansion element assembly 60 comprises a number of expansion blocks 62 disposed symmetrically, radially around the tool body 52, and in the deactivated condition shown in FIG. 2A the blocks are withdrawn into the tool body, but in the activated condition shown in FIG. 2B the blocks are extended beyond the tool body against the wellbore 20.

Figure 3:
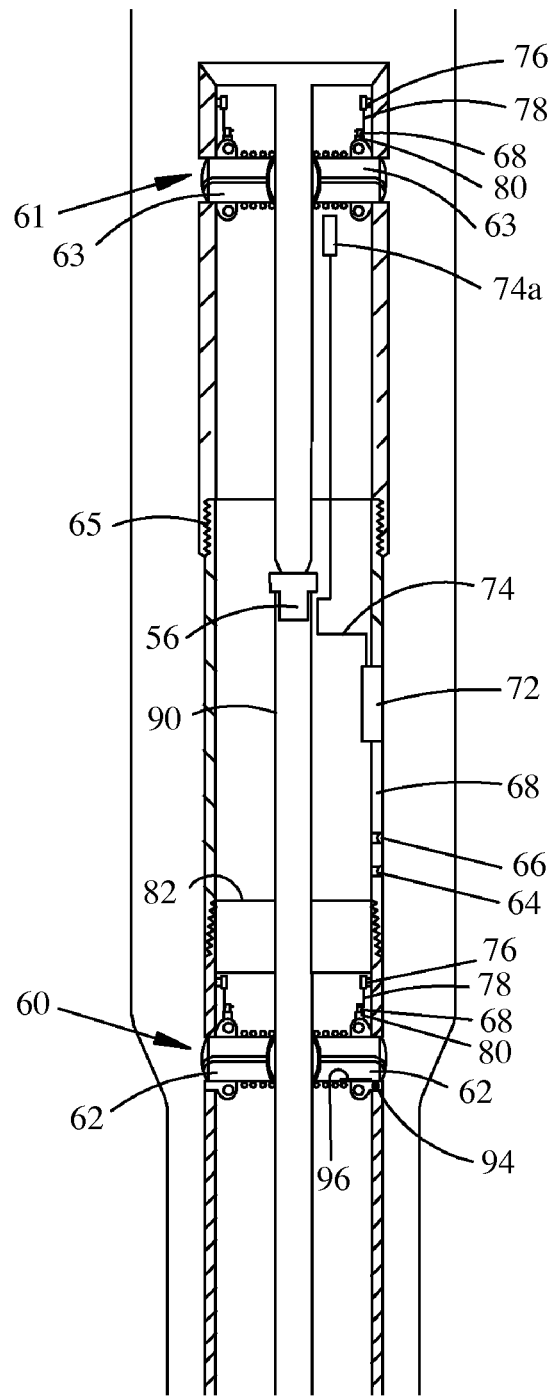
FIG. 3 is a diagrammatic cross section through an underreaming and caliper tool in accordance with the invention similar to that shown in the previous Figures, but having an additional stabiliser section at the trailing uphole end.

FIG. 3 illustrates diagrammatically the aforementioned elements of the tool 50, together with a stabiliser section 61.

Figure 4:
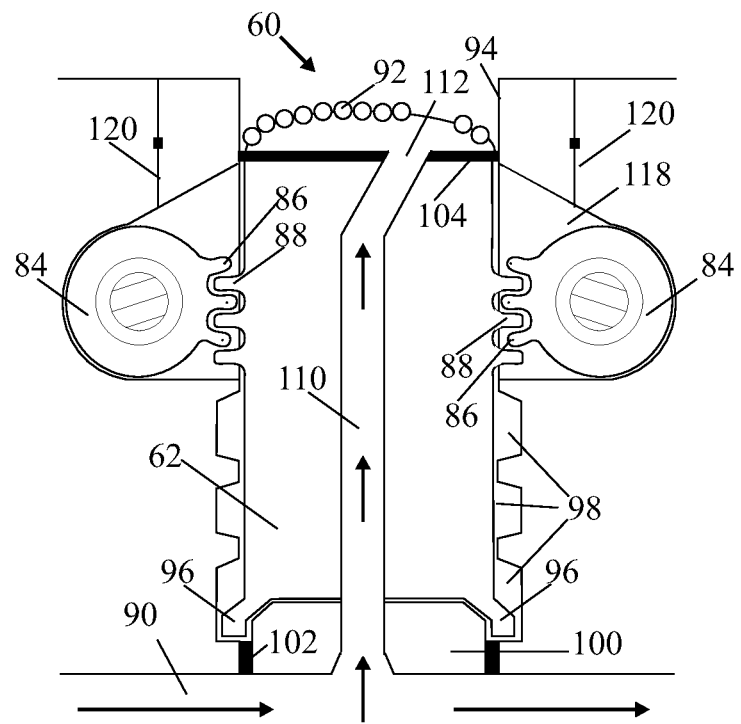
FIG. 4 is an enlargement of part of FIG. 2 showing an expansion block.
Figure 5:
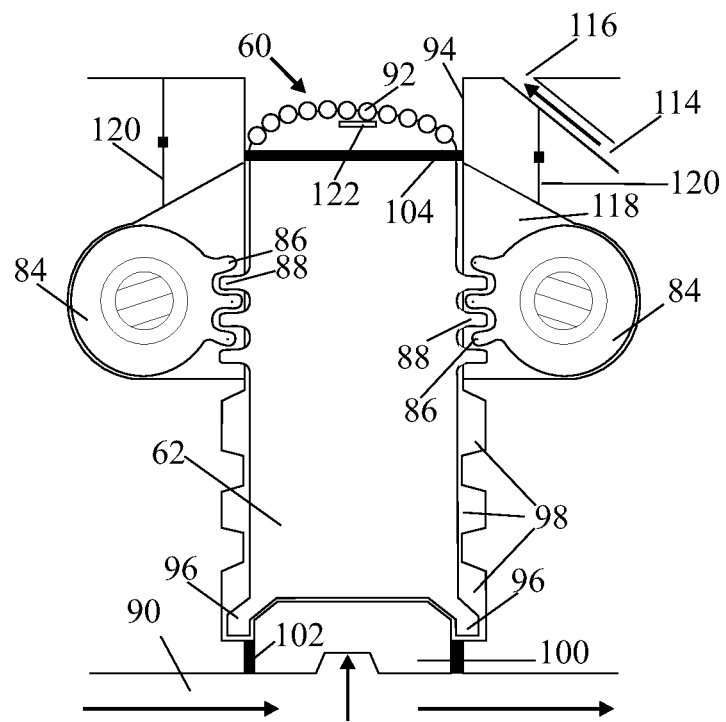
FIG. 5 is a view corresponding to FIG. 4 showing an alternative construction.

FIG. 3 also shows an alternative location for a caliper, in housing 76 connected to wiring in keyway 74 and further wiring 78 to alternative processor location 68 and motor 80 for activation of expansion block 62, as will be further described in relation to FIGS. 4 and 5. FIG. 3 also shows a central axial through passage 90 for the flow of drilling fluid through the whole bottom-hole assembly 40.

A mechanical caliper 122 may be located within the cutter block among the most radially extended cutter elements 92, or on the block surface in the case where the expansion block is not an underreamer with cutting teeth or inserts, but a device for expanding a tubular by deformation.

Housing 76 may also be used for other types of sensor, especially a wellbore vibration sensor to detect a stick-slip condition.

The tool body 52 is a cylindrical high grade steel housing adapted to form part of a bottom-hole assembly (BHA) 40. FIG. 3 shows an internal connection 82 joining two parts of tool body 52. At the leading downhole end of the tool is a section housing the cutter blocks 62. Connection 82 joins this to a central section housing measurement and control functions.

A further section 61 at the uphole end, joined by connection 65, houses stabiliser blocks 63 which are constructed and housed substantially identically to the underreamer components generally designated 60, except that in place of cutter elements on cutter blocks there is at least one surface which is hard faced or coated with a hard abrasion-resistant material. A similar construction can be used to expand a deformable bore, such as a steel tubular. The means for attaching the tool body to a drill string or coiled tubing comprises a screw thread (not shown) provided on the tool body which is engageable with a drill collar (not shown).

In this alternative configuration the tool is configured, in addition to underreaming capacity, with the underreaming tool body incorporating hard facing cutter blocks to act as a stabiliser. The hard facing acts to prevent cutter abrasion while reaming or stabilising the underreamed hole. This eliminates some of the problems associated with loss of directional control due to the undergauge stabiliser above the underreamer.

The stabiliser may be directly or indirectly connected to the underreamer and hard-wired accordingly so as to ensure the mud-pulser may transmit data to surface.

The tool normally comprises a plurality of such cutter blocks 62, arranged symmetrically around the tool. Two cutter blocks are on opposite sides of the tool, three blocks are separated by 120 degrees, four by ninety degrees, and six by sixty degrees. In operation, the underreaming tool 50 is typically rotated on the drill string as well as being moved axially along the wellbore.

FIGS. 4 and 5 show side elevations of cutter blocks (62) with cutter elements or inserts generally designated as 92.

FIG. 4 shows cutter block 62 with internal duct 110 leading to an opening (112) such as a nozzle among cutter elements 92. The nozzle can be located below cutters or recessed as seen by 112 in FIG. 4.

FIG. 5 shows caliper 122 among cutter elements 92.

FIGS. 4 and 5 side views of cutter blocks 62 further correspond to the top view FIG. 11A and frontal view 11B which describe in more detail below cutter patterns, nozzles and caliper location on cutter blocks 62.

Figure 6:
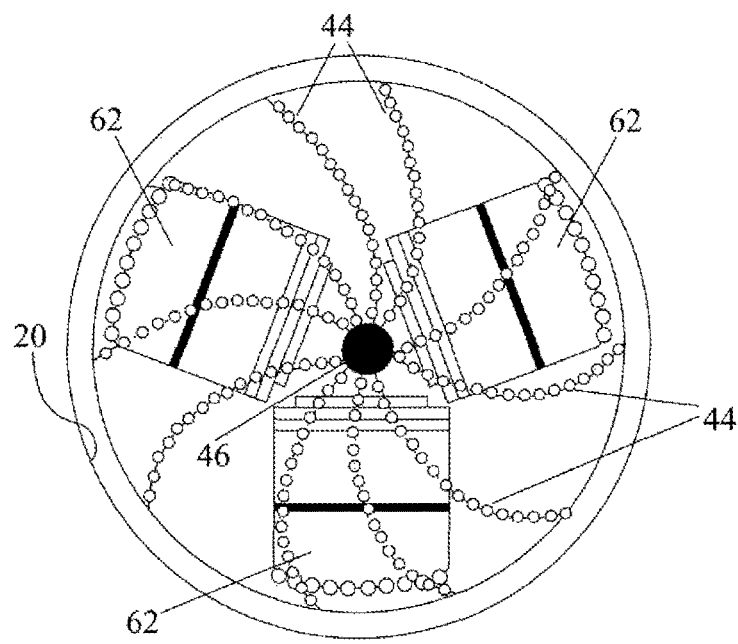
FIG. 6 is a diagram showing cutting elements of the tool positioned in a borehole, the tool being in a deactivated condition.

FIG. 6 illustrates diagrammatically the relationship of the cutter blocks 62 and their cutter elements (inserts 92) with the wellbore 20, before underreaming, and the layout of the teeth on the drill bit.

FIG. 6 superimposes ten curved rows of drill bit teeth 44, as seen from below the BHA looking back up the wellbore, over the cutter block locations. A central drilling fluid outlet 46 indicates where drilling fluid is delivered to the drill bit, having passed through passage 90 in the tool body 52.

Figure 7:
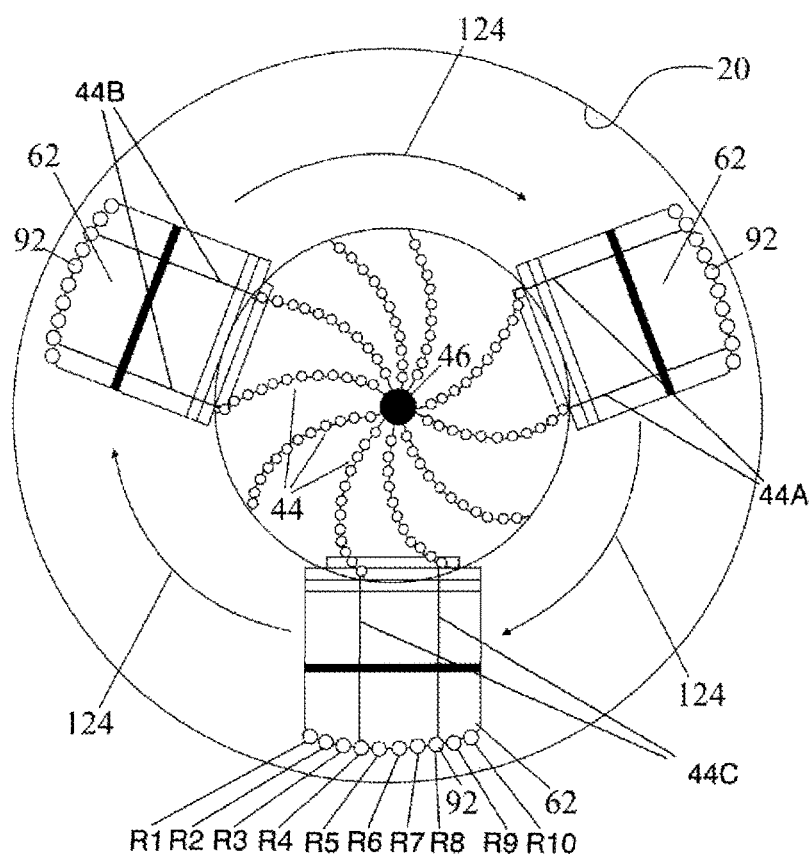
FIG. 7 is a diagram corresponding to FIG. 6 but showing the same elements of the tool when the tool is in an activated condition.

Whereas FIG. 6 illustrates the tool in its deactivated condition, its activated condition with cutter blocks 62 extended and underreaming wellbore 20 is illustrated in FIG. 7. Arrows 124 indicate the sense in which the whole BHA 40, including the curved rows of drill bit teeth 44 and cutter blocks 62, rotate. As the drill deepens the wellbore, so the tool advances towards the viewer, as represented in FIGS. 6 and 7.

Figure 8:
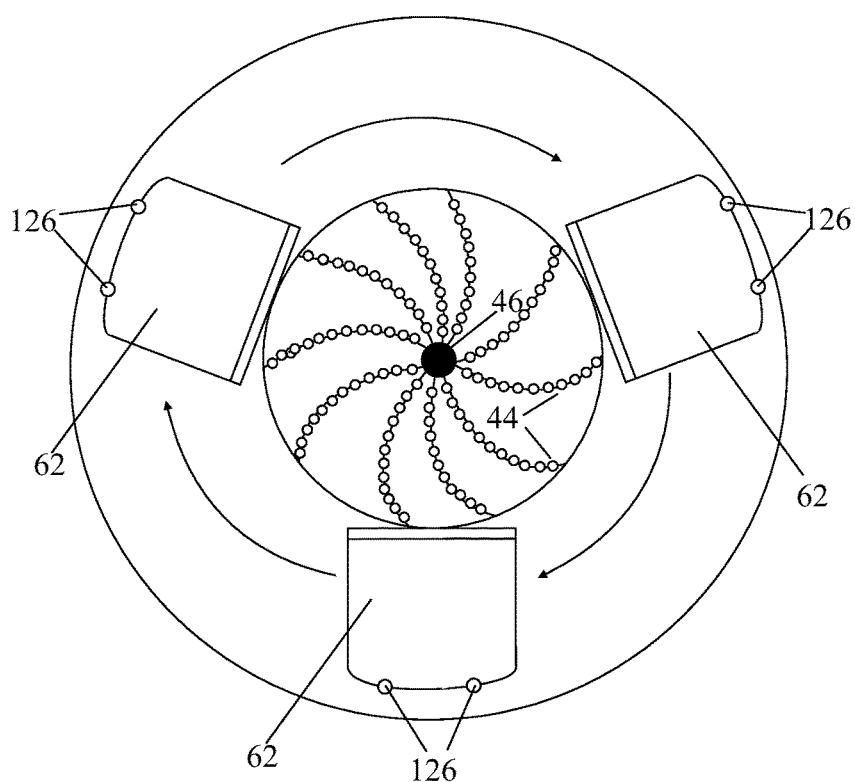
FIG. 8 is a diagram corresponding to FIG. 7 showing the disposition of cutting elements in a notional corresponding prior art approach.

FIG. 8 illustrates a similar operation to that shown in FIG. 7, but with a traditional arrangement of cutting elements (inserts 126) on the cutter blocks. The significance of this will be explained in relation to FIGS. 9A, 9B and 10.

Figure 9A:
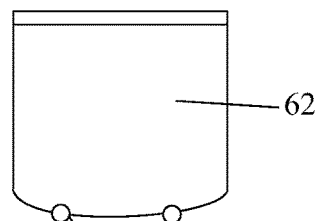
FIG. 9A is a top view and FIG. 9B is a front view of the outer face of a traditional cutter block for underreaming without nozzles and using a vertical arrangement of cutter elements, of the kind illustrated in FIG. 8.
Figure 9B:
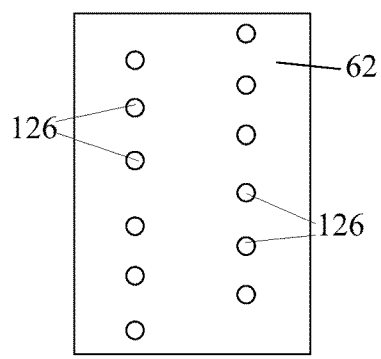
Figure 9B:
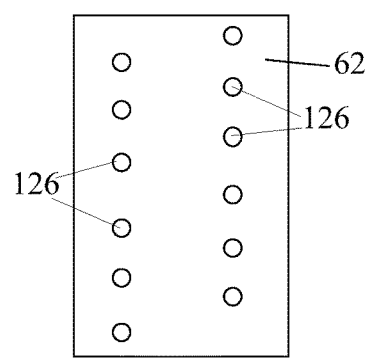

FIG. 9A is a downhole, or equally uphole, profile of a cutter block 62 with a traditional arrangement of cutter elements 126, in two parallel straight lines extending parallel to the bore axis (FIG. 9B). When there are three cutter blocks 62, as in FIG. 8, the underreaming takes place along six parallel lines down the wellbore 20 at any instant.

Figure 10:
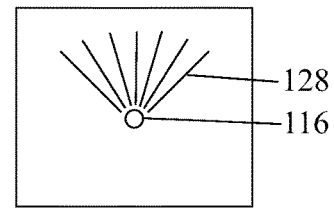
FIG. 10 is a front view corresponding to FIG. 9B showing the placement of a traditional cutting fluid delivery nozzle.

FIG. 10 shows the cutter block face of FIG. 9B together with the traditionally placed drilling fluid nozzle 116; and lines 128 radiating from nozzle 116 indicate the distribution of drilling fluid emerging from the nozzle to lubricate and wash the cutter elements 126.

Figure 11A:
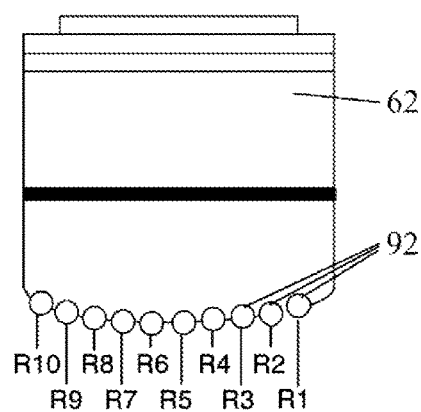
FIGS. 11A and 11B are views of a cutter block in accordance with the invention, corresponding to the views in FIGS. 9A and 9B respectively, showing the tool's cutter block outer face using a helical pattern optimized for underreaming while drilling.
Figure 11B:
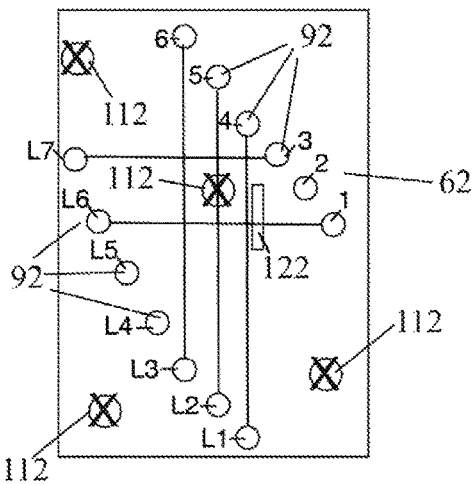

FIGS. 11A and 11B illustrate the improved placement of cutter inserts 92 over the face of each cutter block 62, in accordance with a specific aspect of this invention, and the location of drilling fluid nozzles 112 over the face of the cutter block in accordance with a further specific aspect of this invention. FIGS. 11A and 11B shows the nozzles 112 beside, between, below and adjacent to cutters 92.

FIGS. 6 and 7 respectively show retracted and extended cutter elements (92) placed at different radial angles from a central axial passage (46).

FIG. 11A as viewed from right to left, shows the location of three cutter elements (three lines to circles marked 92) with different radial angles and circumferential points shown as positions (R1, R2 and R3) on the cutter block 62 relative to the central axial passage (46 of FIGS. 6 and 7).

FIG. 11A viewed further from right to left shows three central cutters each placed at differing radial angles (R4, R5 and R6) to the central axis (46) shown in FIG. 7.

FIG. 11B shows rows of cutters 92 across cutter block 62 distributed in circumferential arcs or radial positions shown in FIG. 11A. Each of the three radially central positions of FIG. 11A (R6, R5 and R4) align with at least one cutter element (any of L3, L2 and L1 or 6,5 and 4) which is located at different longitudinal positions as shown in FIG. 11B. FIG. 11B shows two cutter elements located in different longitudinal positions, element (4) and element (L1). FIG. 11B shows cutter elements placed in two longitudinally distant positions yet having the same radial position relative to a central axis (L1 and 4, L2 and 5, L3 and 6). Cutters 92 may be positioned at different or unequal radial positions (R10, R3, R9, R1, R2) or may form circumferential arcs of differing or unequal lengths (L7 and 3, L6 and 1 or 2).

In accordance with the aspect that concerns cutter element placement, it can be seen that these are located in rows extending diagonally across the face of the cutter block, and helically in respect of the wellbore. The helix is oriented in a sense which, as can be seen from consideration of FIGS. 7 and 11 together, corresponds to the path of a screw advancing down the wellbore, although by no means at a corresponding screw pitch and due to the cutter elements may be used to underream upward.

The helix is also in alignment and considered synchronised with the extended outer ends of the rows of teeth 44 on the drill bit, if notionally wrapped in continuation of that alignment around the outside of the BHA 40 extending back as far as the tool body 52.

This provides the advantage that, as can be seen when viewed along the wellbore, the cutter inserts 92 engage the wellbore over a much better circumferentially distributed arc than the six parallel lines of the traditional arrangements, with consequent benefits to equalization of forces around the tool and therefore around the BHA, of which the tool is a part.

In the aspect of cutters contacting the wellbore, FIGS. 6 and 7 show 7 or more points contacting the wellbore, the three cutter blocks (62) show each cutter element (92) is placed at different radial positions (R1-R10) from a central axis or bore (46 which is connected to central axial through passage 90 in the tool).

As will be detailed below FIGS. 11A and 11B show 3 or more points where cutter elements (92) contact the wellbore considering a single expandable block (62).

In the aspect of cutter patterns extending across the face of a cutter block contacting the wellbore with different circumferential arcs or radial positions but the same longitudinal positions, FIG. 11B shows a first cutter (L7) placed in a first radial position (R10 of FIG. 11A) and a second cutter (3) placed in a second radial position (R3 of FIG. 11A) but with the same longitudinal position along the length of the cutter block face; FIG. 11B shows a second cutter (L6) placed at a third radial position (R9 of FIG. 11A) and a fourth cutter (1) placed at a fourth radial position (R1 of FIG. 11A) that is unequally radially spaced with respect to cutters (L7, 3 or L6). FIG. 11B shows that L6 and 1 are placed at the same longitudinal position along the length of the block face. It can be appreciated from FIG. 11B that the radial positions of L7 and 3 form a circumferential arc length that is different and unequal to the circumferential arc length between L6 and 1. FIG. 11B shows cutters with unique radial and longitudinal positions (2, L5 and L4).

In the aspect of cutter patterns extending across the face of a cutter block contacting the wellbore with different longitudinal positions but the same circumferential or radial positions, FIG. 11B shows two cutters (6 and L3) contacting the wellbore at two points having a first circumferential or radial position (6 and L3 correspond to radial position R6 in FIG. 11A). FIG. 11B shows a line drawn between 6 and L3 showing their different longitudinal positions.

FIG. 11B shows a further third and fourth cutter (5 and L2) contacting the wellbore at a further third and fourth point having a second radial position (R5 in FIG. 11A). The line drawn between 5 and L2 shows a different longitudinal position to the first two cutters.

FIG. 11B shows a fifth cutter (either of 4 or L1) contacting the wellbore at a fifth point and placed in a third radial position (R4 in FIG. 11A). The line drawn between 4 and L1 shows either of 4 and L1 are in different longitudinal positions in relation to any the first four cutters (L3, 6, 5 and L2). Each of the radial positions of the pairs of cutters (L1 and 4, L2 and 5, L3 and 6) have different circumferential or radial positions (R4, R5 and R6) respectively.

Further FIG. 11B shows cutters with unique radial and longitudinal positions (2, L5 and L4).

In the aspect of cutter patterns extending across the face of a cutter block with the same radial position but different longitudinal positions, FIG. 11B shows a first pair of cutters (6 and L3) placed in a first radial position (R6 in FIG. 11A) and separated by a longitudinal distance shown by the line between 6 and L3; a second pair of cutters (5 and L2) placed at second radial position (R5 in FIG. 11A) longitudinally offset to the first pair of cutters and a third pair of cutters (4 and L1) placed in a third radial position (R4 in FIG. 11A) longitudinally offset in relation to the first or second pair of cutters (L3 and 6 or 5 and L2).

In a further aspect of cutter patterns extending across the face of a cutter block with a pair of cutters having the same longitudinal position but having different or unequal radial positions, FIG. 11B shows a first row or pair of cutters (L7 and 3) placed at the same longitudinal position and separated by a radial distance (shown as R10 and R3 in FIG. 11A); a second pair of cutters (L6 and 1) placed at different radial positions (shown as R9 and R1 in FIG. 11A) and longitudinally offset relative to the first pair of cutters; and wherein at least one pair of cutters are unequally spaced (FIG. 11A shows either of R10 and R3 or R9 and R1 as unequally spaced) from a central axis or bore (shown as 46 in FIG. 7).

In a related aspect, FIG. 11B shows a first row or pair of cutters (L7 and 3) placed at the same longitudinal position but having different or unequal circumferential arc lengths (the radial distance between R10 and R3 in FIG. 11A defines a circumferential arc) and a second pair of cutters (L6 and 1) placed at different longitudinal positions wherein at least one cutter is spaced at an unequal circumferential arc length (R9 and R1 in FIG. 11A define a different or unequal arc length) relative to a central axis or bore (46).

In a further aspect FIG. 11B shows 3 rows or 3 pairs of radially offset cutters (6 and L3, 5 and L2, 4 and L1) with one or more cutters (L5, L4 or 2) placed in unique radial and longitudinal positions.

In yet a further related aspect FIG. 11B shows swept cutters (L1-L7, 1-6) corresponding to a screw advancing down the wellbore but not a screw pitch. Further cutters (L1-L7 or 1-6) may not be symmetric as viewed along the length and breadth of the cutter block FIG. 11B also shows the placement of the optional mechanical or acoustic caliper 122 on a flat part of the cutter block face between the helical rows of cutter elements 92.

Figure 12:
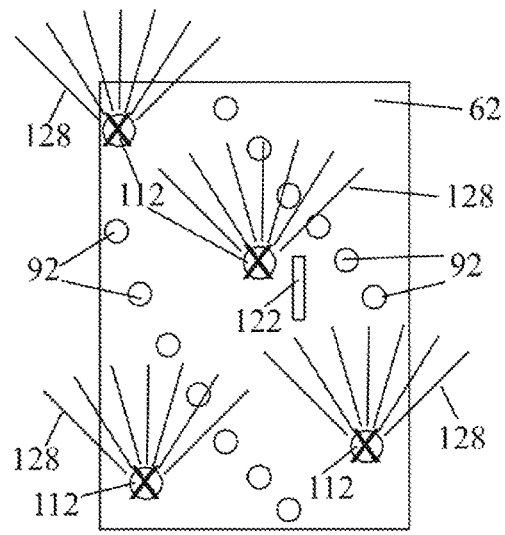
FIG. 12 corresponds to FIG. 10 and shows cutting fluid delivery nozzles located in the cutter block in accordance with the invention.

FIGS. 11B and 12 show the nozzle 112 distribution over the cutter block face. A plurality of nozzles may be provided, and radiating lines 128 again show the drilling fluid distribution, which is now more accurately, usefully and uniformly achieved than in the traditional arrangement of FIG. 10.

Those skilled in the art will appreciate that the examples of the invention given by the specific illustrated and described embodiments show a novel underreaming tool and system and method for underreaming, with numerous variations being possible. These embodiments are not intended to be limiting with respect to the scope of the invention. Substitutions, alterations and modifications not limited to the variations suggested herein may be made to the disclosed embodiments while remaining within the ambit of the invention.

What is claimed is:

1. A bottom hole assembly for use in a wellbore comprising a fixed diameter bit wherein a plurality of cutters extend from a central location to the outer ends of the bit to form a first diameter; and an expandable reamer wherein a further plurality of cutters are placed on an extendable cutter block in at least two substantially parallel substantially helical rows, each substantially helical row having at least tour cutters, wherein at least three of the cutters on one of the substantially helical rows align with three of the cutters on the other of the substantially helical rows along the longitudinal axis to form at least three longitudinal rows of cutters extending along the longitudinal axis of the expandable reamer.

2. The bottom hole assembly of claim 1 further comprising a directional control system.

3. The bottom hole assembly of claim 2 wherein the directional control system is a rotary steerable.

4. The bottom hole assembly of claim 1 wherein cutter placement is optimised to reduce vibration around the bottom hole assembly.

5. The bottom hole assembly of claim 1 further comprising position sensing means.

6. The bottom hole assembly of claim 1 further comprising borehole diameter sensing means.

7. The bottom hole assembly of claim 1 wherein the cutters are hard faced.

8. A method of engaging at least 7 cutters with a wellbore in at least 7 different radial locations by placing cutter elements on one or more extendable cutting blocks in arcuate and longitudinal locations wherein at least eight cutter elements are set in a substantially helical pattern on the extendable cutter block of an expandable reamer and wherein said pattern is repeated in at least two substantially parallel substantially helical rows, wherein each substantially helical row has at least four cutter elements, wherein at least three of the cutter elements on one of the substantially helical rows align with three of the cutter elements on the other of the substantially helical rows along the longitudinal axis to form at least three longitudinal rows of cutters extending along the longitudinal axis of the expandable reamer.

9. The method of claim 8 further comprising a flowpath directly to a reamer cutter face wherein the at least one flowpath is located on the face or middle of a cutter block and radiates flow directly across at least one cutter element.

10. The method of claim 8 further comprising a flowpath directly to a reamer cutter face wherein the at least one flowpath is located on the side of a cutter block and radiates flow directly across at least one cutter element.

11. The method of claim 9 wherein the flow path opens flow between two rows of cutters.

12. The method of claim 8 comprising a rotary steerable.

13. The method of claim 8 comprising a position sensing means.

14. The method of claim 8 comprising a wellbore caliper.

15. An array of cutter elements for drilling an earthen wellbore, wherein at least eight cutter elements are set in a substantially helical pattern on an extendable cutter block of an expandable reamer and wherein said pattern is repeated in at least two substantially parallel substantially helical rows, wherein each substantially helical row has at least four cutter elements, wherein at least three of the cutter elements on one of the substantially helical rows align with three of the cutter elements on the other of the substantially helical rows along the longitudinal axis to form at least three longitudinal rows of cutters extending along the longitudinal axis of the expandable reamer.

16. The array of cutter elements as claimed in claim 15 wherein said cutter elements are set in an expandable cutter block, and preferably set in a plurality of expandable cutter blocks distributed uniformly around the body of a reamer wherein cutter elements form a helix oriented in the direction of reaming.

17. An array of cutter elements as claimed in claim 16 located substantially in rows extending diagonally across the face of the cutter block and helically in respect of the wellbore.

18. An array of cutters as claimed in claim 17 wherein the helix is oriented in the direction of upward reaming.

19. An array of cutters as claimed in claim 16 wherein the helix forms a continuation of outer ends of drill bit teeth.

20. An array of cutters as claimed in claim 16 wherein the helix engages the wellbore in at least 7 different circumferential points.

* * * * *